United States Patent
Heinonen

(10) Patent No.: US 9,610,189 B2
(45) Date of Patent: Apr. 4, 2017

(54) DEVICE IN CONNECTION WITH SLEEP APNEA

(75) Inventor: John Heinonen, Marsta (SE)

(73) Assignee: HEINBERGER AB, Vaxholm (SE)

( * ) Notice: Subject to any disclaimer, the term of this patent is extended or adjusted under 35 U.S.C. 154(b) by 316 days.

(21) Appl. No.: 13/635,442

(22) PCT Filed: Mar. 10, 2011

(86) PCT No.: PCT/SE2011/000046
§ 371 (c)(1),
(2), (4) Date: Sep. 17, 2012

(87) PCT Pub. No.: WO2011/115541
PCT Pub. Date: Sep. 22, 2011

(65) Prior Publication Data
US 2013/0014767 A1  Jan. 17, 2013

(30) Foreign Application Priority Data
Mar. 16, 2010  (SE) ...................................... 1000234

(51) Int. Cl.
*A61F 5/56* (2006.01)
*A61M 16/06* (2006.01)
*A61M 16/04* (2006.01)

(52) U.S. Cl.
CPC .......... *A61F 5/566* (2013.01); *A61M 16/049* (2014.02); *A61M 16/0666* (2013.01); *A61M 16/0683* (2013.01)

(58) Field of Classification Search
CPC ... A61F 5/566; A61M 16/06; A61M 16/0666; A61M 16/493

USPC .............. 128/848, 859–862, 204.18, 206.29, 128/207.18, 201.26; 602/902
See application file for complete search history.

(56) References Cited

U.S. PATENT DOCUMENTS

| | | | | |
|---|---|---|---|---|
| 5,537,994 A | * | 7/1996 | Thornton | 128/204.18 |
| 5,752,510 A | * | 5/1998 | Goldstein | 128/207.18 |
| 5,954,048 A | * | 9/1999 | Thornton | 128/201.18 |
| 5,983,892 A | * | 11/1999 | Thornton | 128/201.26 |
| 6,012,455 A | * | 1/2000 | Goldstein | 128/207.18 |
| 6,209,542 B1 | * | 4/2001 | Thornton | 128/206.29 |

(Continued)

FOREIGN PATENT DOCUMENTS

| | | |
|---|---|---|
| AU | 766684 | 10/2003 |
| WO | 98/20924 | 5/1998 |
| WO | 2007/084940 | 7/2007 |

OTHER PUBLICATIONS

International Search Report dated Jun. 10, 2011, corresponding to PCT/SE2011/00046.

*Primary Examiner* — Kari Petrik
*Assistant Examiner* — Raymond E Harris
(74) *Attorney, Agent, or Firm* — Young & Thompson

(57) ABSTRACT

A device in connection with sleep apnoea, includes a dental splint (1) designed to engage with the jaws of the user in the position of use of the device and the device moreover includes elements (10, 11) for delivering air to the nostrils of the user from an external air source and a holder element (3) for supporting the elements (10, 11) for the delivery of air, the holder element (3) being connected to the dental splint (1). The holder element (3) is connected to the dental splint (1) by way of elements (7, 9) for adjusting the distance between the dental splint (1) and the holder element (3).

11 Claims, 6 Drawing Sheets

(56) References Cited

U.S. PATENT DOCUMENTS

| | | | |
|---|---|---|---|
| 6,374,824 B1* | 4/2002 | Thornton | 128/201.26 |
| 6,405,729 B1* | 6/2002 | Thornton | 128/848 |
| 6,571,798 B1* | 6/2003 | Thornton | 128/206.21 |
| 7,311,103 B2* | 12/2007 | Jeppesen | 128/201.26 |
| 7,562,659 B2* | 7/2009 | Matarasso | 128/207.18 |
| 8,607,796 B2* | 12/2013 | Thornton | 128/848 |
| 2004/0025884 A1* | 2/2004 | McKown | 128/207.18 |
| 2006/0207597 A1* | 9/2006 | Wright | 128/206.11 |
| 2008/0276938 A1* | 11/2008 | Jeppesen et al. | 128/204.18 |
| 2010/0224197 A1* | 9/2010 | Keropian | 128/848 |

* cited by examiner

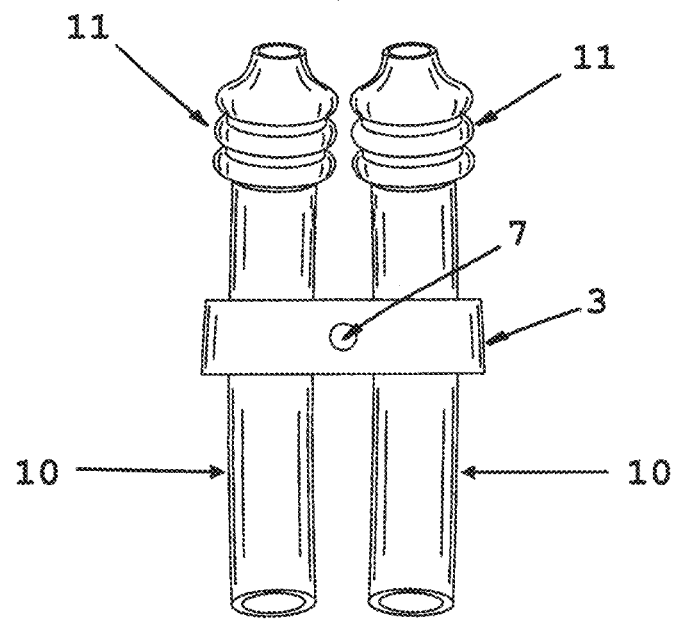
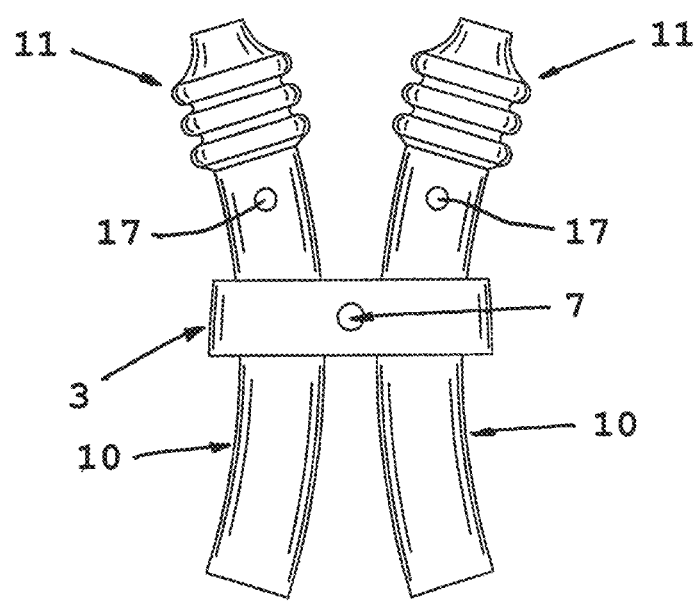

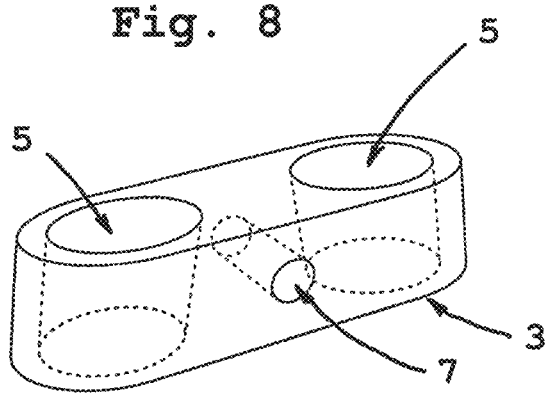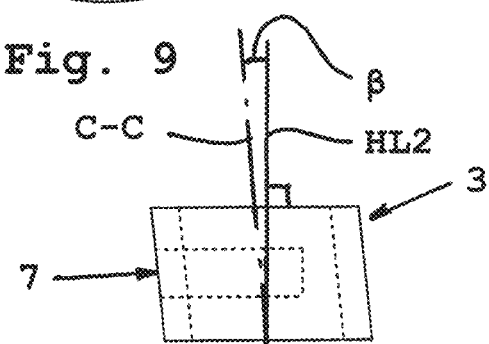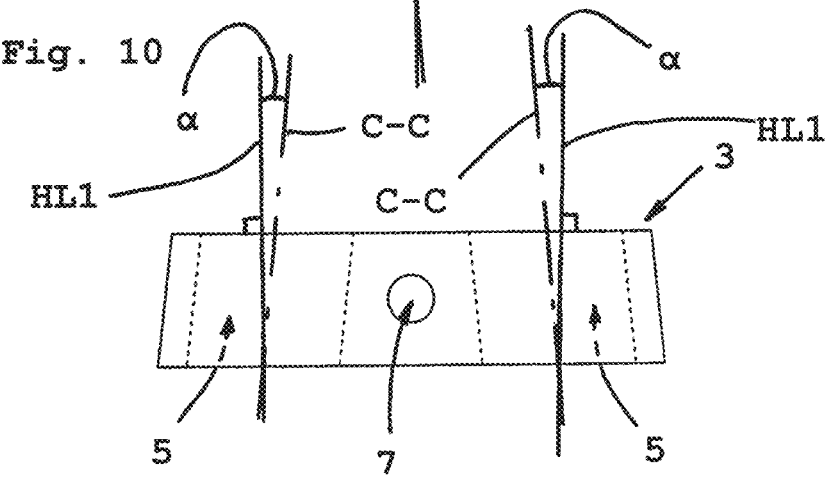

DEVICE IN CONNECTION WITH SLEEP APNEA

TECHNICAL FIELD OF THE INVENTION

This invention relates to a device in connection with sleep apnea, wherein the device includes a dental splint designed to engage with the jaws of the user in the position of use of the device and the device moreover includes means for delivering air to the nostrils of the user from an external air source and a holder element for supporting the means for the delivery of air, the holder element being connected to the dental splint, that the holder element is connected to the dental splint by means that allow adjustment of the distance between the dental splint and the holder element, that the holder element is equipped with through-going holes, and that the means for the delivery of air are received in these holes.

STATE OF THE ART

From WO 2007/084940 a device in connection with sleep apnea is previously known, said device comprising a dental splint and tubes for supplying air to the nostrils of the user. The part of the tubes that extends through the holder element is straight and the upper end of the straight parts connects to the nostrils of the user. Hoses are connected to the lower end of the straight parts.

From U.S. Pat. No. 6,571,798 a device in connection with sleep apnea is previously known, said device comprising a dental splint and straight tubes for supplying air to the nostrils of the user. The tubes extend between a holder element and the nostrils of the user.

From U.S. Pat. No. 5,752,510 an apparatus for alleviation of breathing disorders is previously known, said apparatus involving tubes for air delivery, said tubes having a slight arcuation. The tubes are adjustable and by means of a knob the adjustment to the user is carried out.

U.S. Pat. No. 6,012,455 discloses an apparatus for delivering air to the nose, the apparatus including a dental splint designed to receive the upper jaw and the lower jaw. Flexible tubes extend between a platform connected to the dental splint and the nostrils of the wearer.

U.S. Pat. No. 5,537,994 discloses a mask for improved breathing during sleep. The mask includes double dental splints and a link element which can be removably attached to one of the dental splints. The mask itself is adjustably connected to the element.

AIMS AND FEATURES OF THE INVENTION

A first aim of this invention is to provide a device of the type defined in the introductory part, wherein the device offers good adjustment options from the point of view of individual adaptation to the user.

Another aim of this invention is for the device to have a simple design and for the device to consist at least partly of standard components.

Yet another aim of this invention is to allow the device to be anchored in a satisfactory manner in the jaw of the user.

At least the first aim of this invention is achieved by means of a device having the features specified in independent claim 1 hereinafter. Preferred embodiments of the invention are defined in the dependent claims.

BRIEF DESCRIPTION OF THE DRAWINGS

A preferred embodiment of the invention will now be described with reference to the accompanying drawings, in which:

FIG. 4 is a front view of the device according to this invention in which the tubes to be connected to the nostrils of the user are substantially parallel in the view shown;

FIG. 5 is a corresponding front view to that of FIG. 4, in which the tubes to be connected to the nostrils of the user diverge in an upward direction;

FIG. 8 is a perspective view of a holder element forming part of the device according to this invention;

FIG. 9 is a side view of the holder element according to FIG. 8;

FIG. 10 is a front view of the holder element according to FIG. 8;

DETAILED DESCRIPTION OF A PREFERRED EMBODIMENT OF THE INVENTION

Figure 1:
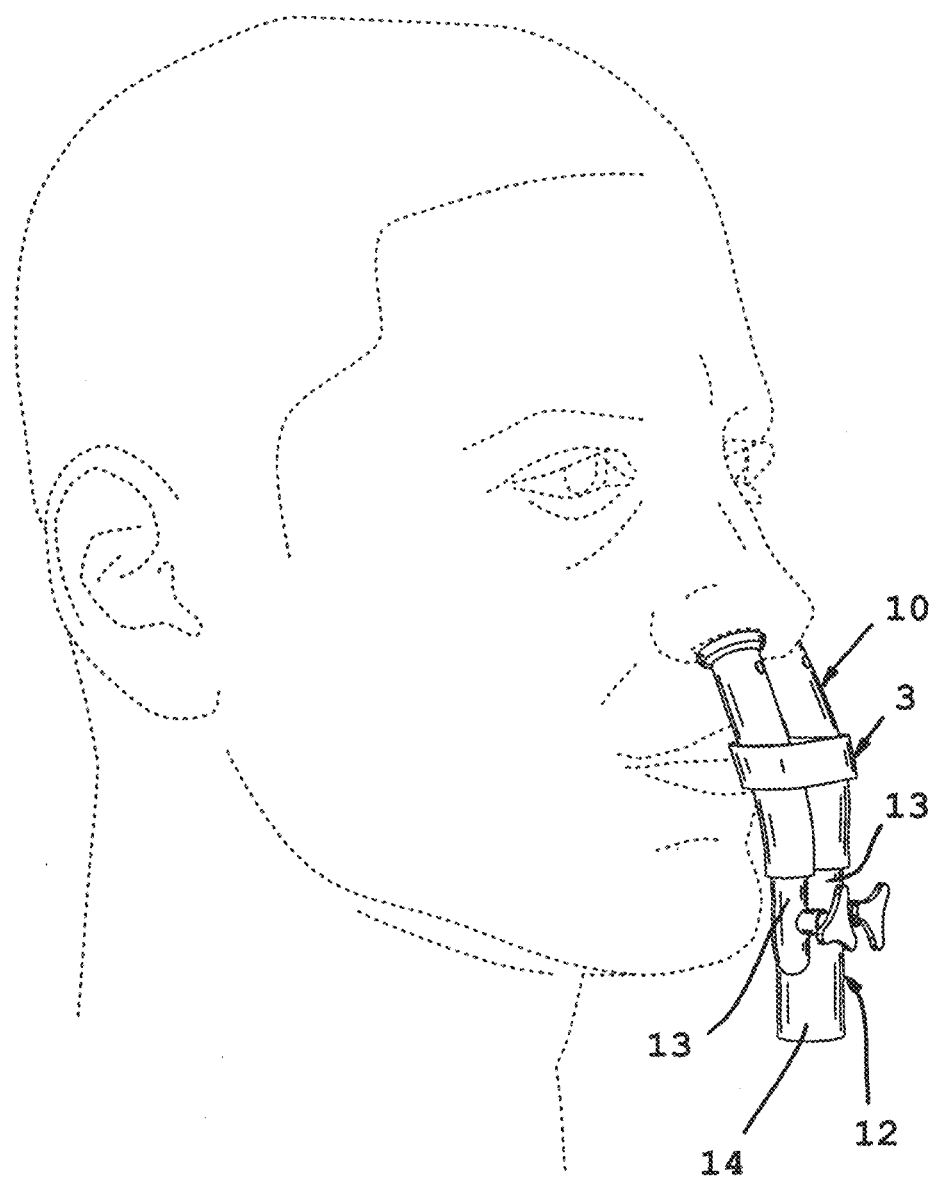
FIG. 1 is a perspective view in which the device is worn by a user.

The device according to this invention shown in FIGS. 1-7 includes a dental splint 1 and a holder element 3, the dental splint 1 and the holder element 3 being connected together by means of an externally threaded stud bolt 9 permanently connected to the dental splint 1. This is shown most clearly in FIGS. 6 and 7.

The dental splint 1 defines an upper space for receiving the upper jaw of the user and a lower space for receiving the lower jaw of the user.

The holder element 3, which forms an important part of the device according to this invention, is shown in detail in FIGS. 8-10. As will be clear from FIGS. 8-10, the holder element 3 is provided with two first through holes 5 traversing the top and underside of the holder element. When the holder element 3 is viewed from the front, the holes converge in an upward direction. As will be clear from FIG. 10, the center axes C-C of the first holes 5 form an angle $\alpha$ with first auxiliary lines HL1 parallel to one another. The angle $\alpha$ should be within the range $6° \leq \alpha \leq 10°$.

As will be clear from FIG. 9, the first holes 5 are also inclined when the holder element 3 is viewed from the side, although the first holes 5 then display the same degree of inclination and are inclined in the same direction. The inclination of the first holes 5 in the plane of the drawing in FIG. 9 is defined by the center axes C-C of the first holes. The inclination of the first holes 5 relative to a second auxiliary line HL2 is designated by the angle $\beta$, wherein the value of $\beta$ should be within the range $3° \leq \beta \leq 7°$. The second auxiliary line HL2 is parallel to the first auxiliary lines HL1. According to the embodiment shown, all of the auxiliary lines HL1, HL2 are at a right angle to the top and underside of the holder element 3.

The holder element 3 also comprises a cavity 7 extending partly into the holder element 3 according to the embodiment shown. In general, the cavity 7 extends transversely to the first holes 5. The cavity 7 is internally threaded. It can be mentioned by way of a non-limiting example that a polyester-based urethane rubber sold under the name Elathane® has proven to be a suitable material for the holder element 3. A Shore hardness of 95 A has proven to be a suitable hardness for the material.

Figure 11:
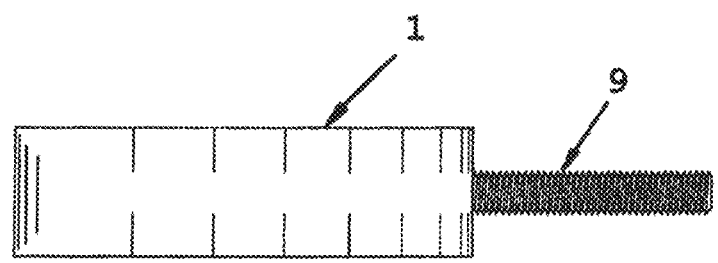
FIG. 11 is a side view of a dental splint and an externally threaded stud bolt, these components forming part of the device according to this invention.
Figure 12:
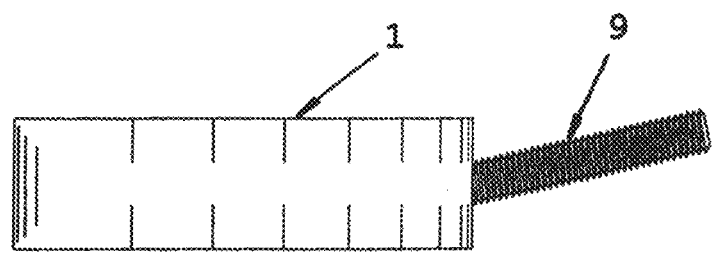
FIG. 12 is a side view of a dental splint and an externally threaded stud bolt, the stud bolt being disposed at a different angle relative to the dental splint from that shown in FIG. 11.

FIGS. 11 and 12 show a side view of the dental splint 1, wherein an externally threaded stud bolt 9 is permanently anchored to the front part of the dental splint 1, i.e. the part situated at the very front of the mouth of the user when the dental splint 1 is in an active position. As will be clear from FIGS. 11 and 12, the stud bolt 9 can be disposed at an angle relative to the dental splint 1. In FIG. 11, the stud bolt 9 in principle extends in such a manner that it coincides with the extension of the dental splint 1. In FIG. 12, the stud bolt 9 is angled upwards in the direction of the free end of the stud bolt 9. The anchoring of the stud bolt 9 in the dental splint 1 shown in FIGS. 11 and 12 is shown only by way of example. The stud bolt 9 may of course be anchored in other positions, although it is preferably situated between the positions shown in FIGS. 11 and 12. The dental splint 1 is preferably adapted to the anatomy of the individual user.

Figure 3:
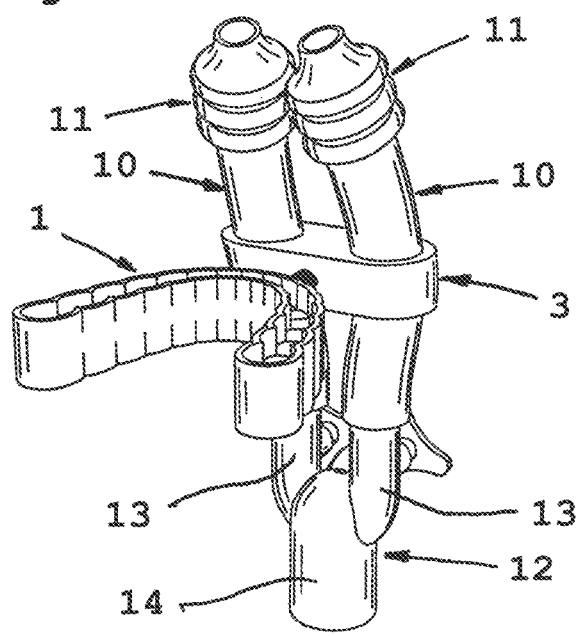
FIG. 3 is a perspective view of the device according to FIG. 2 from the opposite direction.
Figure 6:
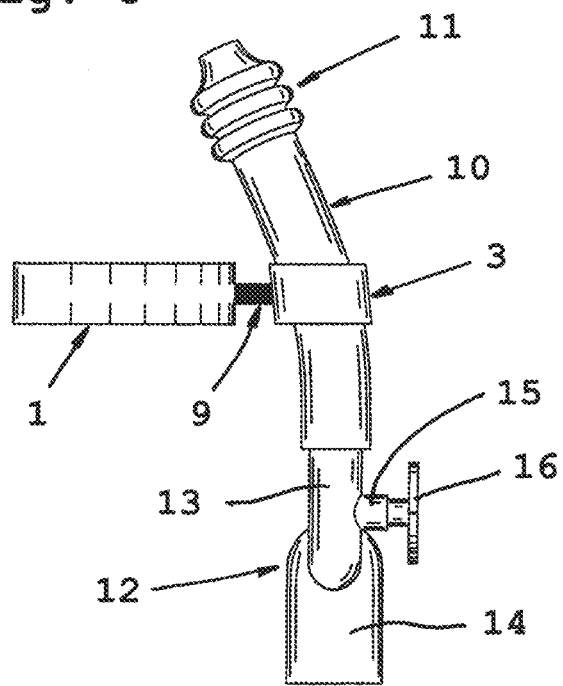
FIG. 6 is a side view of the device according to this invention in which the dental splint is situated at a certain distance from a holder element forming part of the device according to this invention.
Figure 7:
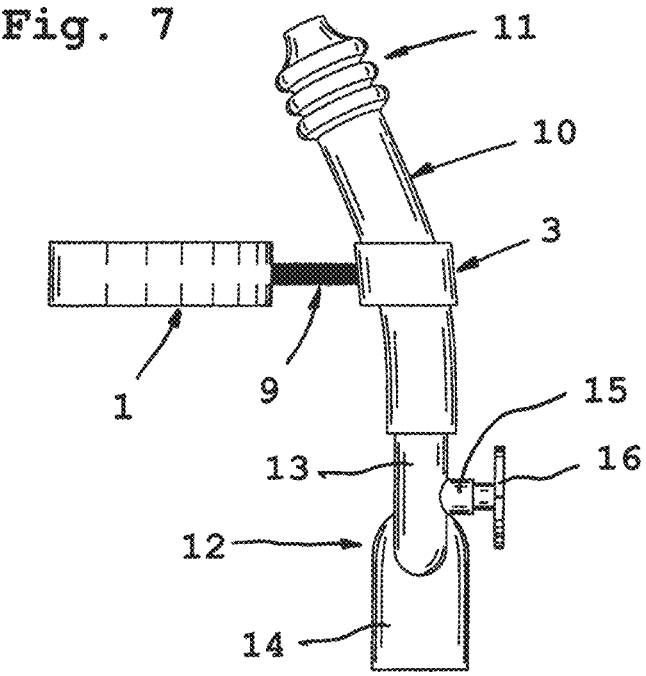
FIG. 7 is a corresponding side view to that of FIG. 6, but with the dental splint situated at a greater distance from the holder element.

As will be seen most clearly from FIGS. 3, 6 and 7, the stud bolt 9 is received in the cavity 7 in the holder element 3, the stud bolt 9 being screwed into the cavity 7. This of course presupposes that the dimensions of the cavity 7 and the stud bolt 9 are adapted to one another. The cavity 7 is not normally provided from the outset with an internal thread, but an internal thread is created in the cavity 7 when the stud bolt is screwed in for the first time. FIGS. 6 and 7 show that the stud bolt 9 can be screwed into the cavity 7 to varying degrees, this being important from the point of view of being able to adapt the device to the individual user. Displacement of the stud bolt 9 in the cavity 7 is achieved by mutual rotation of the dental splint 1 and the holder element 3.

As will be clear from FIGS. 1-7, two air delivery tubes 10 are received in the holder element 3, these tubes 10 displaying a certain radius of curvature. It can be mentioned by way of a non-limiting example that the radius of curvature of the tubes 10 should be between 20 cm and 30 cm. It will be clear from FIGS. 1-7 that the tubes 10 have substantially the same longitudinal extent above and below the holder element 3. The tubes 10 are continuously rotatable relative to the holder element 3. The tubes 10 can also be displaced continuously in their longitudinal direction relative to the holder element 3 so as to allow for individual setting of the width between the nostrils and of the distance between the nose and the holder element 3.

Nasal pads 11 are applied to the upper ends of the tubes 10 and are received in the nostrils of the user when the device according to this invention is in use. The tubes 10 are preferably provided at their upper ends with a bead/thickened portion (not shown) promoting the anchoring of the nasal pads 11 at the upper ends of the tubes. As will be seen most clearly from FIGS. 6 and 7, the tubes 10 are normally oriented in such a manner that their upper ends extend inwardly towards the dental splint 1. This is ensured partly by the inclination of the through holes 5.

As will be clear from FIGS. 1-7, the lower ends of the tubes 10 are connected to a branch piece 12 provided at the top with two first tube connectors 13, wherein the lower ends of the tubes 10 are supposed to be connected to these first tube connectors 13. The branch piece 12 is also provided at the bottom with a second tube connector 14, wherein a hose from a CPAP apparatus is supposed to be connected to the second tube connector 14. CPAP stands for "Continuous Positive Airway Pressure". The CPAP apparatus delivers compressed air to the device according to this invention.

According to the embodiment shown, the branch piece 12 is provided with two valves 15 for delivering extra oxygen as required. The valves 15 can also be used for the connection of suitable measuring equipment. The valves 15 are located on the two first tube connectors 13. The valves 15 are moreover closed by means of stoppers 16 when the valves 15 are not in use.

FIG. 1 shows how the device according to this invention is applied to a user. The dental splint 1 is inserted into the oral cavity of the user and the user puts his upper jaw and lower jaw in the respective spaces provided in the dental splint 1. The holder element 3 is then situated immediately in front of the mouth of the user. The upper ends of the tubes 10, together with the nasal pads 11, are received in the nostrils of the user.

As each person/user is unique from the point of view of the proportions of the face, e.g. from the point of view of the distance between the mouth and the nose, the width between the nostrils, etc., it is extremely important that the device according to this invention allows for individual adaptation/setting and that this setting can be carried out in a simple manner. For an explanation of how adaptation/setting of this kind is carried out, reference should be made to FIGS. 4 and 5, showing a front view of the holder element 3 with the air delivery tubes 10.

In FIG. 4, the tubes 10 are oriented in such a manner that they are substantially parallel to one another. It can be concluded from the appearance of the lower ends of the tubes 10 that the curvature of the tubes 10 is substantially in a plane at right angles to the plane of the drawing.

In FIG. 5, the tubes 10 are oriented in such a manner in the holder element 3 that the distance between the adjacent ends of the tubes 10 is greater than the distance between the parts of the tubes 10 received in the holder element 3. The curvature of the tubes 10 is substantially in the plane of the drawing in FIG. 5.

Looking at FIGS. 4 and 5, it will be clear that the distance between the ends of the tubes 10 can be varied by rotating the tubes 10 relative to the holder element 3. FIGS. 4 and 5 show only two examples of how the tubes 10 can be oriented relative to the holder element 3. As the tubes 10 can be continuously rotated, raised and lowered relative to the holder element 3, it is in principle possible to obtain a large number of positions with respect to the orientation of the tubes 10 relative to the holder element 3.

Figure 2:
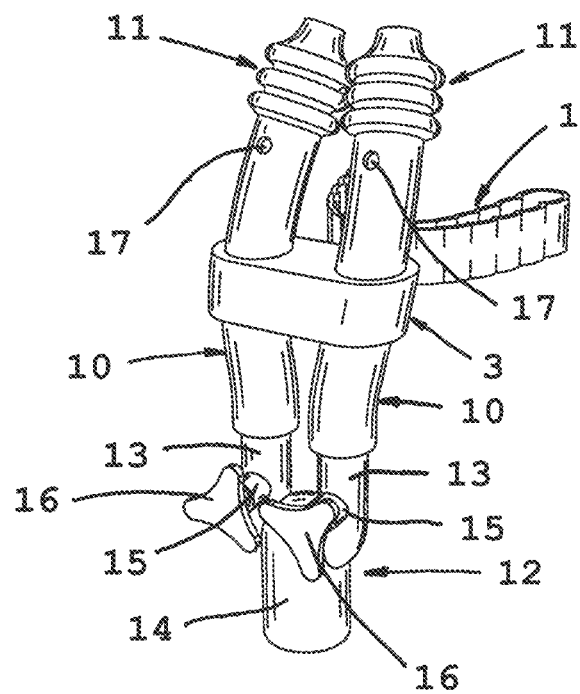
FIG. 2 is a perspective view of the device according to this invention.

As shown, e.g. in FIGS. 2 and 3, the lower ends of the tubes 10 are supposed to be connected to the first tube connectors 13 of the branch piece 12. As the first tube connectors 13 are situated at a uniform distance from one another, this means that the distance between the lower ends of the tubes 10 must be the same as this uniform distance when the lower ends of the tubes 10 are connected to the tube connectors 13. If it is assumed that the distance between the lower ends of the tubes 10 in FIG. 5 is greater than the uniform distance between the first tube connectors 13, the lower ends of the tubes 10 must be brought towards one another so that they can be connected to the first tube connectors 13. This means that the distance between the upper ends of the tubes 10 increases as the material in the holder element 3 displays a certain flexibility. If the distance between the upper ends of the tubes 10 is too great, the lower ends of the tubes 10 must be released from the first tube connectors 13 and the tubes 10 rotated once again into a new position relative to the holder element 3. After a number of attempts, the desired distance between the upper ends of the tubes 10 is achieved, i.e. this distance corresponds to the distance between the nostrils of the user. In order to obtain the correct "depth" setting, i.e. so that the upper ends of the tubes 10 are not situated too far inside or outside the nostrils of the user, the distance between the dental splint 1 and the holder element 3 can be adjusted. As described hereinabove, this is effected in that the stud bolt 9 is screwed to a greater or lesser degree into the cavity 7. Displacement of the stud bolt 9 in the cavity 7 is effected by mutual rotation of the dental splint 1 and the holder element 3.

When the tubes 10 are set in their final positions, a second hole 17 is provided in each of the tubes 10, more precisely in the region of the upper ends of the tubes 10, the second holes 17 being directed away from the face of the user. These second holes 17 are vent holes ensuring that the air delivered to the user has a suitable oxygen content.

When the device according to this invention is worn by a user in the manner illustrated in FIG. 1 and the branch piece 12 is connected to a CPAP apparatus, compressed breathing air is delivered to the user via the tubes 10, the nasal pads 14 and the nostrils of the user.

POSSIBLE MODIFICATIONS OF THE INVENTION

The holder element 3 described hereinabove includes two first through holes 5, the inclination of the holes 5 partly relative to one another and partly relative to auxiliary lines HL1 and HL2 being described hereinabove. However, according to this invention, it may be conceivable for the first through holes to be parallel to one another. It may also be conceivable for the holes to be parallel to the auxiliary lines. As the air delivery tubes 10 display a certain radius of curvature, there are still adjustment options even when the holder element 3 is designed in the manner last defined.

The invention claimed is:

1. A sleep apnea device, comprising:
    a dental splint (1) that engages with jaws of a user in a position of use;
    an adjusting means (7, 9);
    a holder element (3) connected to the dental splint via the adjusting means, the adjusting means being adjustable to vary a distance between the dental splint (1) and the holder element (3);
    two air delivery tubes (10) that connect to an external air source and deliver air to nostrils of the user from the external air source, the two air delivery tubes being supported by the holder element (3),
    wherein the holder element (3) comprises through holes (5), the air delivery tubes (10) are received in the through holes (5) extending i) below a first lower side of the holder element (3), ii) through the through holes (5) in a longitudinal direction such that the air delivery tubes (10) are spaced apart in a transverse direction in the holder element (3) by a fixed first distance and uppermost ends of the two air delivery tubes (10) are spaced apart in the transverse direction by a variable second distance, and iii) out from an upper second side of the holder element (3), the air delivery tubes (10) have a non-zero radius of curvature in a portion passing through the holes (5) and extending above the holes (5), the air delivery tubes (10) are rotatable within the through holes (5) relative to the holder element (3), and the air delivery tubes (10) are displaceable in the longitudinal direction within the through holes (5) relative to the holder element (3) to thereby change the second distance between the uppermost ends of the two air delivery tubes (10) in the transverse direction,
    wherein the adjusting means (7, 9) includes a threaded stud bolt (9) and an internally threaded cavity (7), and the threaded stud bolt (9) is received in the internally threaded cavity (7), and
    wherein the threaded stud bolt (9) is permanently connected to the dental splint (1) and the internally threaded cavity (7) is received in the holder element (3).

2. The sleep apnea device according to claim 1, wherein, with the device on the user, in a side view of the holder element (3), center axes (C-C) of the through holes (5) are inclined inwardly towards the user in a direction of the nostrils of the user.

3. The sleep apnea device according to claim 2, wherein the adjusting means (7, 9) includes a threaded stud bolt (9) and an internally threaded cavity (7), and the threaded stud bolt (9) is received in the internally threaded cavity (7).

4. The sleep apnea device according to claim 2, wherein the radius of curvature of the air delivery tubes (10) is between 20 cm and 30 cm.

5. The sleep apnea device according to claim 1, wherein, with the device on the user, in a front view of the holder element (3), center axes (C-C) of the through holes (5) converge in a direction of the nostrils of the user.

6. The sleep apnea device according to claim 5, wherein the adjusting means (7, 9) includes a threaded stud bolt (9) and an internally threaded cavity (7), and the threaded stud bolt (9) is received in the internally threaded cavity (7).

7. The sleep apnea device according to claim 1, wherein the air delivery tubes (10) comprise upper ends provided with beads/thickened portions.

8. The sleep apnea device according to claim 1, wherein nasal pads (11) are applied to upper ends of the air delivery tubes (10).

9. The sleep apnea device according to claim 1, wherein the air delivery tubes (10) are provided with vent holes (17) in a region of their upper ends.

10. A sleep apnea device, comprising:
    a dental splint (1) with an upper space for receiving an upper jaw of a user and a lower space for receiving a lower jaw of the user such that, in use, the dental splint engages with the upper and lower jaws of a user;
    an adjusting means (7, 9) connected to the dental splint;
    a holder element (3) connected to the dental splint via the adjusting means, the holder element (3) comprising through holes (5) that, when the holder element is viewed from a front side, the through holes converge in an upward direction; and
    two air delivery tubes (10) displacable received in the through holes (5) of the holder element (3) such that the air delivery tubes (10) are spaced apart in a transverse direction in the holder element (3) by a fixed first distance and uppermost ends of the two air delivery tubes (10) are spaced apart in the transverse direction by a variable second distance, the two air delivery tubes (10) extending i) below a first lower side of the holder element (3), ii) in a longitudinal direction through the through holes (5), and iii) out from an upper second side of the holder element (3), the air delivery tubes (10) arranged to deliver air from an external air source to nostrils of the user,
    wherein the adjusting means is adjustable to vary a distance between the dental splint (1) and the holder element (3), wherein the air delivery tubes (10) have a non-zero radius of curvature in a portion passing through the holes (5) and extending above the holes (5), wherein the air delivery tubes (10) are rotatable within the through holes (5) relative to the holder element (3), and the air delivery tubes (10) are displaceable in the longitudinal direction within the through holes (5) relative to the holder element (3) to thereby change the second distance between the uppermost ends of the two air delivery tubes (10) in the transverse direction, wherein the adjusting means (7, 9) includes a threaded stud bolt (9) and an internally threaded cavity (7), and the threaded stud bolt (9) is received in the internally threaded cavity (7), and wherein the threaded stud bolt (9) is permanently connected to the dental splint (1) and the internally threaded cavity (7) is received in the holder element (3).

11. The sleep apnea device according to claim 10, wherein the radius of curvature of the air delivery tubes (10) is between 20 cm and 30 cm.

\* \* \* \* \*